(12) United States Patent
Li

(10) Patent No.: US 8,570,531 B2
(45) Date of Patent: Oct. 29, 2013

(54) METHOD OF REGENERATING DIFFRACTION SIGNALS FOR OPTICAL METROLOGY SYSTEMS

(75) Inventor: Shifang Li, Pleasanton, CA (US)

(73) Assignee: Tokyo Electron Limited, Tokyo (JP)

( * ) Notice: Subject to any disclaimer, the term of this patent is extended or adjusted under 35 U.S.C. 154(b) by 220 days.

(21) Appl. No.: 13/316,521

(22) Filed: Dec. 11, 2011

(65) Prior Publication Data

US 2013/0151440 A1   Jun. 13, 2013

(51) Int. Cl.
*G01B 11/24* (2006.01)

(52) U.S. Cl.
USPC .......................................... 356/601

(58) Field of Classification Search
USPC .......................... 356/601, 606, 607
See application file for complete search history.

(56) References Cited

U.S. PATENT DOCUMENTS

| | | | |
|---|---|---|---|
| 6,785,638 B2 | 8/2004 | Niu et al. | |
| 6,891,626 B2 | 5/2005 | Niu et al. | |
| 6,943,900 B2 | 9/2005 | Niu et al. | |
| 7,064,829 B2 | 6/2006 | Li et al. | |
| 7,271,902 B2 | 9/2007 | Li et al. | |
| 7,280,229 B2 | 10/2007 | Li et al. | |
| 7,302,367 B2 | 11/2007 | Li et al. | |
| 7,388,677 B2 | 6/2008 | Vuong et al. | |
| 7,450,232 B2 | 11/2008 | Li et al. | |
| 7,477,405 B2 * | 1/2009 | Finarov et al. | 356/625 |
| 7,617,075 B2 | 11/2009 | Li et al. | |
| 7,660,696 B1 * | 2/2010 | Norton et al. | 702/151 |
| 7,831,528 B2 | 11/2010 | Doddi et al. | |
| 2004/0109173 A1 * | 6/2004 | Finarov et al. | 356/625 |
| 2005/0192914 A1 | 9/2005 | Drege et al. | |
| 2010/0007885 A1 | 1/2010 | Li et al. | |
| 2010/0010765 A1 | 1/2010 | Li et al. | |
| 2011/0245955 A1 * | 10/2011 | Li et al. | 700/104 |
| 2011/0246141 A1 | 10/2011 | Li et al. | |
| 2011/0246142 A1 | 10/2011 | Li et al. | |
| 2011/0246400 A1 * | 10/2011 | Li | 706/12 |

OTHER PUBLICATIONS

U.S. Appl. No. 12/050,053, filed Mar. 17, 2008 for Tian, et al.
U.S. Appl. No. 13/316,438, filed Dec. 9, 2011 for Li et al.

* cited by examiner

*Primary Examiner* — Roy M Punnoose
(74) *Attorney, Agent, or Firm* — Manual B Madriaga

(57) ABSTRACT

Provided is a method for enhancing accuracy of an optical metrology system that includes a metrology tool, an optical metrology model, and a profile extraction algorithm. The optical metrology model includes a model of the metrology tool and a profile model of the sample structure, the profile model having profile parameters. A library comprising Jones and/or Mueller matrices and/or components (JMMOC) and corresponding profile parameters is generated using ray tracing and a selected range of beam propagation parameters. An original simulated diffraction signal is calculated using the optical metrology model. A regenerated simulated diffraction signal is obtained using the regenerated JMMOC, integrated for all the rays of the optical metrology model. If an error and precision criteria for the regenerated simulated diffraction signal compared to the original simulated diffraction signal are met, one or more profile parameters are determined from the best match regenerated simulated diffraction signal.

20 Claims, 13 Drawing Sheets

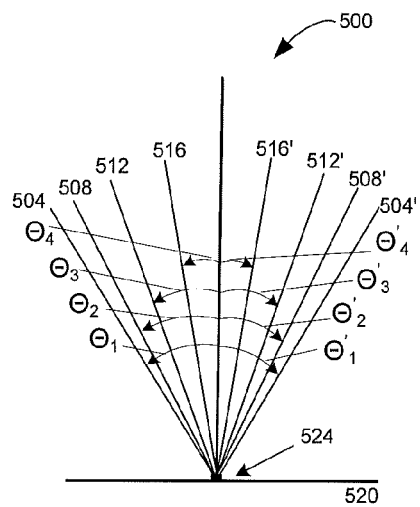
FIG. 5
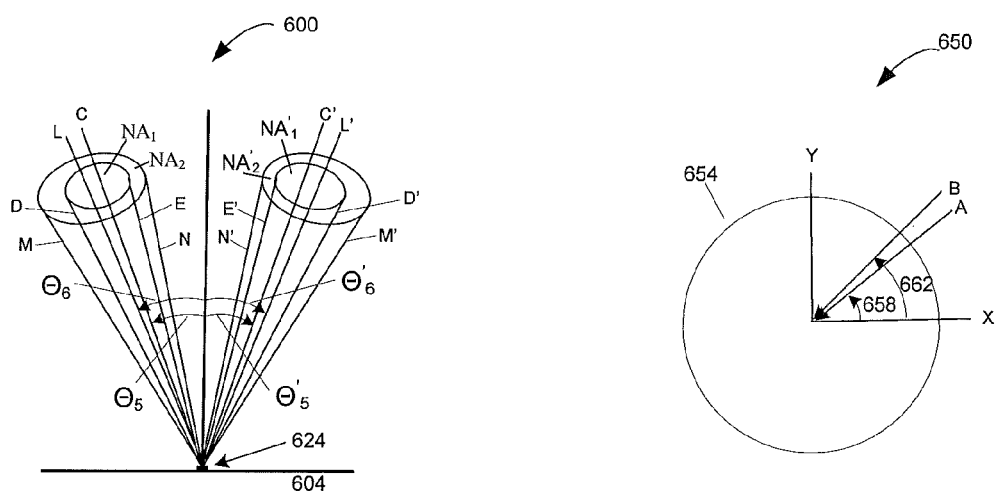
FIG. 6A
FIG. 6B

METHOD OF REGENERATING DIFFRACTION SIGNALS FOR OPTICAL METROLOGY SYSTEMS

BACKGROUND

1. Field

The application generally relates to the use of an optical metrology system to measure a sample structure formed on a workpiece, and, more particularly, to a method and a system for regenerating diffraction signal optical metrology systems.

2. Related Art

Optical metrology involves directing an incident beam at a sample structure on a workpiece, measuring the resulting diffraction signal, and analyzing the measured diffraction signal to determine various characteristics of the sample structure. The workpiece can be a wafer, a substrate, photomask or a magnetic medium. In manufacturing of the workpieces, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured diffraction signal) is compared to a library of diffraction signals. Each diffraction signal in the library is associated with a hypothetical profile. When a match is made between the measured diffraction signal and one of the diffraction signals in the library, the hypothetical profile associated with the diffraction signal is presumed to represent the actual profile of the periodic grating. The hypothetical profiles, which are used to generate the diffraction signals, are generated based on a profile model that characterizes the structure to be examined. Thus, in order to accurately determine the profile of the sample structure using optical metrology, a profile model that accurately characterizes the sample structure should be used.

With increased requirements for throughput, smaller size of the test structures, smaller spot sizes, and lower cost of ownership, there is greater need to optimize design of optical metrology systems to meet the objectives of the overall application. Current optical metrology systems typically focus on optimizing the variables used in generating the simulated diffraction signals. Accuracy requirements increase as the dimensions of the structures get smaller, for example, as the lithography node goes to 30 nm and smaller. In terms of measurement uncertainty, as the size of the structures get smaller, complicated interactions between the optical metrology tool properties vary in complex ways to affect the accuracy of the measurement. For example, as the lithography node gets smaller, errors associated with critical dimension and sample structure profile extraction are the larger errors to be considered. With a smaller lithography node, the total measurement uncertainty and other characterization of uncertainty need to be considered with all elements that can contribute to the error in the measured signal off the structure. As the size of the structures get smaller, factors that did not substantially affect the measurement accuracy are now making an impact.

Furthermore, assumptions used in modeling the optical metrology tool are no longer sufficient. In order to achieve enhanced accuracy of profile parameters of the structure, considerations regarding the physical optics, geometric optics, beam propagation parameters, and detail analysis of the effect of imperfections of optical elements on the illumination and diffraction beam paths need to be incorporated in the modeling and simulations of the diffraction signal to be used in a profile parameter extraction system.

In ray tracing, when the number of rays is increased, the length of time to create a library and the size of the library can be problematic. As the numerical aperture (NA) is increased, the size of the library is also increased. For training a machine learning systems (MLS), time for training the MLS increases as the number of the training samples used to train the MLS increases. The use of reflection coefficients and Jones matrix further increases the size of the library, thus the time needed for MLS training can be a significant consideration. Some of the simulated diffraction signals can be pre-calculated and averaged before recording or training the MLS. However, the library or MLS is dependent on the specific system calibration parameters. Thus, there is a need for a library with a reasonable size while maintaining the accuracy of the optical metrology system for determining profile parameters of the sample structure. Furthermore, there is a need for an optical metrology system that has the flexibility to handle metrology applications with different system calibration parameters, different ray tracing techniques, different beam propagation parameters, different diffraction metrology signal parameters (metrology signal parameters) while maintaining reasonable response times for integrated or standalone metrology applications.

SUMMARY

Provided is a method for enhancing accuracy of an optical metrology system that includes a metrology tool, an optical metrology model, and a profile extraction algorithm. The optical metrology model includes a model of the metrology tool and a profile model of the sample structure, the profile model having profile parameters. A library comprising Jones and/or Mueller matrices and/or components (JMMOC) and corresponding profile parameters is generated using ray tracing and a selected range of beam propagation parameters. An original simulated diffraction signal is calculated using the optical metrology model. A regenerated simulated diffraction signal is obtained using the regenerated JMMOC, integrated for all the rays of the optical metrology model. If an error and precision criteria for the regenerated simulated diffraction signal compared to the original simulated diffraction signal are met, one or more profile parameters are determined from the best match regenerated simulated diffraction signal.

BRIEF DESCRIPTION OF DRAWINGS

FIG. 5 depicts an exemplary architectural diagram illustrating use of ray tracing model with varying number of rays.

FIG. 6A depicts an exemplary architectural diagram illustrating use of ray tracing model with varying numerical aperture (NA).

FIG. 6B depicts an exemplary architectural diagram illustrating use of ray tracing model with a varying azimuth angle.

DETAILED DESCRIPTION

In order to facilitate the description of the present invention, a semiconductor wafer or substrate may be utilized to illustrate an application of the concept. The systems and processes equally apply to other workpieces that have repeating structures. The workpiece may be a wafer or substrate, a substrate, disk, or the like. Furthermore, in this application, the term structure when it is not qualified refers to a patterned structure. Moreover, the term structure and sample structure are used interchangeably and refer to the same item. The sample structure can be a grating, a three-dimensional repeating structure, or the like.

Figure 1:
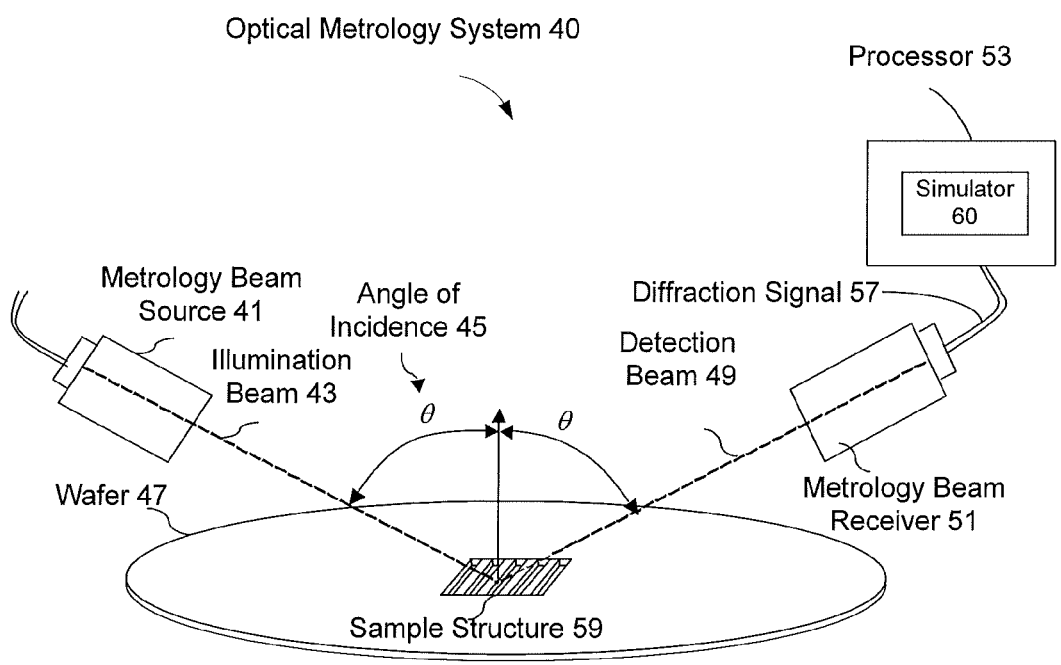
FIG. 1 is an architectural diagram illustrating an exemplary embodiment where an optical metrology system can be utilized to determine the profiles of structures formed on a semiconductor wafer, substrate, or workpiece.

FIG. 1 is an architectural diagram illustrating an exemplary embodiment where optical metrology can be utilized to determine the profiles or shapes of structures fabricated on a semiconductor wafer or substrate. The optical metrology system 40 includes a metrology beam source 41 projecting a metrology illumination beam 43 at the sample structure 59 of a wafer or substrate 47. The metrology illumination beam 43 is projected at an incidence angle 45 (θ) towards the sample structure 59. The diffracted detection beam 49 is measured by a metrology beam receiver 51. A measured diffraction signal 57 is transmitted to a processor 53. The processor 53 compares the measured diffraction signal 57 against simulated diffraction signals of a simulator 60 and associated hypothetical profiles representing varying combinations of critical dimensions of the sample structure and resolution. The simulator can be either a library that consists of a machine learning system, pre-generated data base and the like (a library system), or on demand diffraction signal generator that solves the Maxwell equation for a giving profile (a regression system). In one exemplary embodiment, the diffraction signal generated by the simulator 60 best matching the measured diffraction signal 57 is selected. The hypothetical profile and associated critical dimensions of the selected simulator 60 are assumed to correspond to the actual cross-sectional shape and critical dimensions of the features of the sample structure 59. The optical metrology system 40 may utilize a reflectometer, an ellipsometer, or other optical metrology device to measure the diffraction beam or signal. An optical metrology system is described in U.S. Pat. No. 6,943,900, entitled GENERATION OF A LIBRARY OF PERIODIC GRATING DIFFRACTION SIGNAL, issued on Sep. 13, 2005, which is incorporated herein by reference in its entirety.

Simulated diffraction signals can be generated by applying Maxwell's equations and using a numerical analysis technique to solve Maxwell's equations. It should be noted that various numerical analysis techniques, including variations of rigorous coupled-wave analysis (RCWA), can be used. For a more detail description of RCWA, see U.S. Pat. No. 6,891,626, entitled CACHING OF INTRA-LAYER CALCULATIONS FOR RAPID RIGOROUS COUPLED-WAVE ANALYSES, filed on Jan. 25, 2001, issued on May 10, 2005, which is incorporated herein by reference in its entirety.

Simulated diffraction signals can also be generated using a machine learning system (MLS). Prior to generating the diffraction signals, the MLS is trained using known input and output data. In one exemplary embodiment, simulated diffraction signals can be generated using an MLS employing a machine learning algorithm, such as back-propagation, radial basis function, support vector, kernel regression, and the like. For a more detailed description of machine learning systems and algorithms, see U.S. Pat. No. 7,831,528, entitled OPTICAL METROLOGY OF STRUCTURES FORMED ON SEMICONDUCTOR WAFERS USING MACHINE LEARNING SYSTEMS, filed on Jun. 27, 2003, and issued on Nov. 9, 2010, which is incorporated herein by reference in its entirety.

Figure 2:
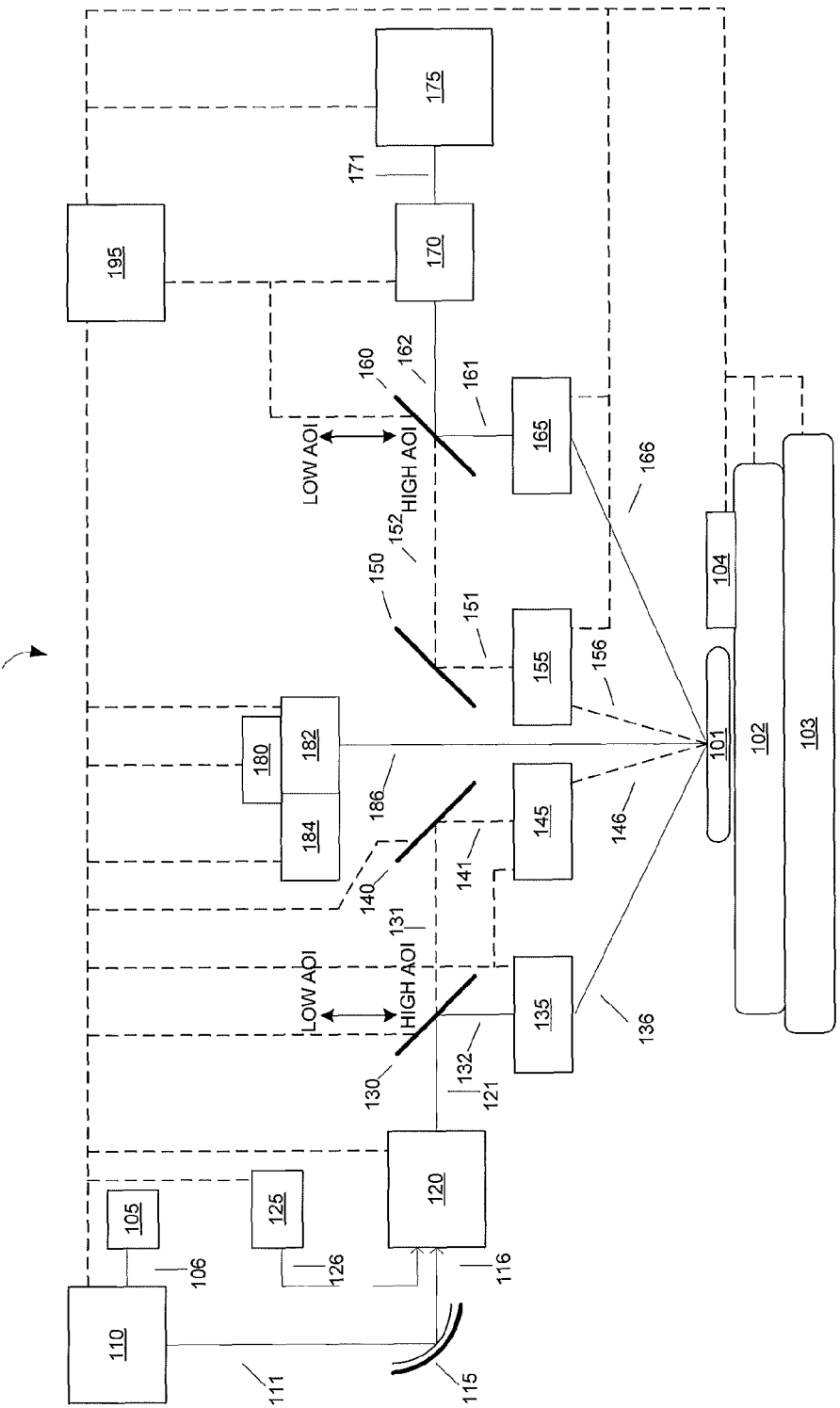
FIG. 2 depicts an exemplary optical metrology system in accordance with embodiments of the invention.

FIG. 2 shows an exemplary block diagram of an optical metrology system in accordance with embodiments of the invention. In the illustrated embodiment, an optical metrology system 100 can comprise a lamp subsystem 105, and at least two optical outputs 106 from the lamp subsystem can be transmitted to an illuminator subsystem 110. At least two optical outputs 111 from the illuminator subsystem 110 can be transmitted to a selector subsystem 115. The selector subsystem 115 can send at least two signals 116 to a beam generator subsystem 120. In addition, a reference subsystem 125 can be used to provide at least two reference outputs 126 to the beam generator subsystem 120. The wafer 101 is positioned using an X-Y-Z-theta stage 102 where the wafer 101 is adjacent to a wafer alignment sensor 104, supported by a platform base 103.

The optical metrology system 100 can comprise a first selectable reflection subsystem 130 that can be used to direct at least two outputs 121 from the beam generator subsystem 120 on a first path 131 when operating in a first mode "LOW AOI" (AOI, Angle of Incidence) or on a second path 132 when operating in a second mode "HIGH AOI". When the first selectable reflection subsystem 130 is operating in the first mode "LOW AOI", at least two of the outputs 121 from the beam generator subsystem 120 can be directed to a first reflection subsystem 140 as outputs on the first path 131, and at least two outputs 141 from the first reflection subsystem can be directed to a high angle focusing subsystem 145. When the first selectable reflection subsystem 130 is operating in the second mode "HIGH AOI", at least two of the outputs 121 from the beam generator subsystem 120 can be directed to a low angle focusing subsystem 135 as outputs on the second path 132. Alternatively, other modes in addition to "LOW AOI" and "HIGH AOI" may be used and other configurations may be used.

When the metrology system 100 is operating in the first mode "LOW AOI", at least two of the outputs 146 from the high angle focusing subsystem 145 can be directed to the wafer 101. For example, a high angle of incidence can be used. When the metrology system 100 is operating in the second mode "HIGH AOI", at least two of the outputs 136 from the low angle focusing subsystem 135 can be directed to the wafer 101. For example, a low angle of incidence can be used. Alternatively, other modes may be used and other configurations may be used.

The optical metrology system 100 can comprise a high angle collection subsystem 155, a low angle collection subsystem 165, a second reflection subsystem 150, and a second selectable reflection subsystem 160.

When the metrology system 100 is operating in the first mode "LOW AOI", at least two of the outputs 156 from the wafer 101 can be directed to the low angle collection subsystem 155. For example, a low angle of incidence can be used. In addition, the low angle collection subsystem 155 can process the outputs 156 obtained from the wafer 101 and low angle collection subsystem 155 can provide outputs 151 to the second reflection subsystem 150, and the second reflection subsystem 150 can provide outputs 152 to the second selectable reflection subsystem 160. When the second selectable reflection subsystem 160 is operating in the first mode "LOW AOI" the outputs 152 from the second reflection subsystem 150 can be directed to the analyzer subsystem 170. For example, at least two blocking elements can be moved allowing the outputs 152 from the second reflection subsystem 150 to pass through the second selectable reflection subsystem 160 with a minimum amount of loss.

When the metrology system 100 is operating in the second mode "HIGH AOI", at least two of the outputs 166 from the wafer 101 can be directed to the high angle collection subsystem 165. For example, a high angle of incidence can be used. In addition, the high angle collection subsystem 165 can process the outputs 166 obtained from the wafer 101 and high angle collection subsystem 165 can provide outputs 161 to the second selectable reflection subsystem 160. When the second selectable reflection subsystem 160 is operating in the second mode "HIGH AOI" the outputs 162 from the second selectable reflection subsystem 160 can be directed to the analyzer subsystem 170.

When the metrology system 100 is operating in the first mode "LOW AOI", low incident angle data from the wafer 101 can be analyzed using the analyzer subsystem 170, and when the metrology system 100 is operating in the second mode "HIGH AOI", high incident angle data from the wafer 101 can be analyzed using the analyzer subsystem 170.

Metrology system 100 can include at least two measurement subsystems 175. At least two of the measurement subsystems 175 can include at least two detectors such as spectrometers. For example, the spectrometers can operate from the Deep-Ultra-Violet to the visible regions of the spectrum.

Those skilled in the art will recognize that at least two of the subsystems (105, 110, 115, 120, 125, 130, 135, 140, 145, 150, 155, 160, 165, 170, 175, and 195) can include computers and memory components (not shown) as required. For example, the memory components (not shown) can be used for storing information and instructions to be executed by computers (not shown) and may be used for storing temporary variables or other intermediate information during the execution of instructions by the various computers/processors in the metrology system 100. At least two of the subsystems (105, 110, 115, 120, 125, 130, 135, 140, 145, 150, 155, 160, 165, 170, 175, 190, and 195) can include the means for reading data and/or instructions from a computer readable medium and can comprise the means for writing data and/or instructions to a computer readable medium. The metrology system 100 can perform a portion of or all of the processing steps of the invention in response to the computers/processors in the processing system executing at least two sequences of at least two instructions contained in a memory and/or received in a message. Such instructions may be received from another computer, a computer readable medium, or a network connection. In addition, at least two of the subsystems (105, 110, 115, 120, 125, 130, 135, 140, 145, 150, 155, 160, 165, 170, 175, and 190 can comprise control applications, Graphical User Interface (GUI) components, and/or database components.

It should be noted that the beam when the metrology system 100 is operating in the first mode "LOW AOI" with a low incident angle data from the wafer 101 all the way to the measurement subsystems 175, (output 166, 161, 162, and 171) and when the metrology system 100 is operating in the second mode "HIGH AOI" with a high incident angle data from the wafer 101 all the way to the measurement subsystems 175, (output 156, 151, 152, 162, and 171) is referred to as diffraction signal(s).

Figure 3:
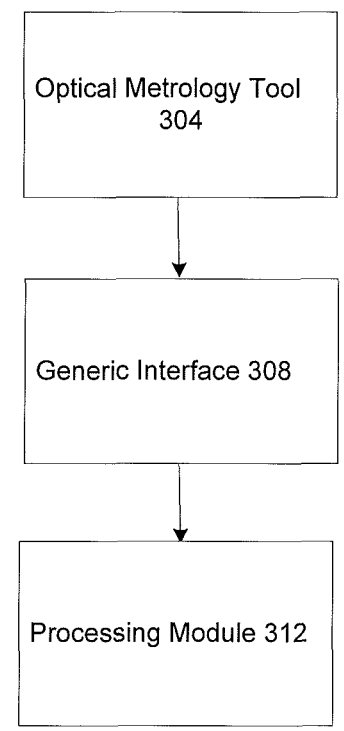
FIG. 3 depicts a prior art optical metrology system flowchart for a generic interface disposed between an optical metrology tool and a processing module.

FIG. 3 depicts a prior art architectural diagram of an optical metrology system for a generic interface disposed between an optical metrology tool such as a photometric device and a processing module. Optical metrology tool 304 includes a light source configured to generate and direct light onto a sample structure, and a detector configured to detect light diffracted from the sample structure and to convert the detected light into a measured diffraction signal. The processing module 312 is configured to receive the measured diffraction signal from optical metrology tool 304, and more particularly the detector, to analyze the structure, such as determining the profile of the structure.

Various types of photometric devices can be used, which provide measured diffraction signals using various metrology signal parameters. A generic interface 308 is configured to provide the measured signal to processing module 312 using a standard set of metrology signal parameters. The standard set of metrology signal parameters includes a reflectance parameter that characterizes the change in intensity of light when reflected on the structure, and polarization parameters that characterizes the change in polarization states of light when reflected on the structure. When an optical metrology tool 304 is a reflectometer that only measures the change in the intensity of light, such as a spectrometric reflectometer, generic interface 308 provides the measured diffraction signal to processing module 312 using only the reflectance parameter of the standard set of metrology signal parameters. When optical metrology tool 304 is an ellipsometer that measures both the change in the intensity of light and polarization states of light, such as a rotating compensator ellipsometer (RCE), generic interface 308 provides the measured diffraction signal to processing module 312 using the reflectance parameter (or reflectivity), and the polarization parameter of the standard set of metrology signal parameters or the harmonics of the diffracted signal with respect to the modulation.

Photometric devices used in optical metrology of semiconductor structures typically use focused beams to produce small spot sizes (in the order of µm). Thus, for a photometric device that uses a focused beam, the measured diffraction signal is the integration of the measured diffraction signals corresponding to all the pencil rays in the effective numerical aperture (NA) of the photometric device. Each ray of the set of rays in the NA corresponds to a specific angle of incidence (AOI) and wavelength. Additionally, the square of the absolute value of the complex reflection coefficients (CRCs), $r_s$ and $r_p$, are functions of angle of incidence (AOI). Because of the dependence on AOI, the focusing beam is depolarized.

For an exemplary photometric device, the measured diffraction signals can be characterized by the following relationship:

$$I = PSD \cdot M \cdot PSG \quad (1)$$

where PSD is the row vector representing the response of the polarization state detector to the Stokes parameters of polarized light, PSG is the column vector representing Stokes parameters of the light created by the polarization generator, and M is the Mueller matrix. For a specific ray in the principal plane (with given AOI and wavelength), the Mueller matrix of the sample at classical mount can be written as:

$$M(AOI, \lambda) = \begin{pmatrix} Rp + Rs & Rp - Rs & 0 & 0 \\ Rp - Rs & Rp + Rs & 0 & 0 \\ 0 & 0 & \mathrm{Re}(Rsp) & \mathrm{Im}(Rsp) \\ 0 & 0 & -\mathrm{Im}(Rsp) & \mathrm{Re}(Rsp) \end{pmatrix} \quad (2)$$

where Rs, $p = |r_{s,p}|^2$, $Rsp = r_s r_p^*$ and $r_s$, $r_p$ are the complex reflection coefficients. When the grating is not setup at classical mount, there are cross polarization terms, and the Muller matrix becomes a full matrix.

For a photometric device using a focused beam, the measured diffraction signals are the intensity integration of all the pencil rays over the NA and detector bandwidth around the center wavelength of the photometric device. This integration can be done solely for the Mueller matrix formula as follows:

$$I = \int I(AOI, \lambda) d\Omega_{AOI} d\lambda \approx PSD \cdot (\int M(AOI, \lambda) d\Omega_{AOI} d\lambda) \cdot PSG \quad (3)$$

The photometric device may measure the center wavelengths one at a time, or measure all center wavelengths in parallel. The interface and signal processing module may convert and process the measured spectra when data for a portion of the center wavelengths is available, or after the data of all center wavelengths is available.

Thus, the measured diffraction signals can be characterized as:

$$I \approx PSD \cdot (RM') \cdot PSG \quad (4)$$

where R is the quantity to describe average intensity change at the sample structure, and M' is the Normalized Muller matrix that describes the polarization change of the light reflected at the sample structure. As mentioned above, as the size of the structures get smaller, factors that did not substantially affect the measurement accuracy are now making an impact. Furthermore, assumptions used in modeling the optical metrology tool are no longer sufficient. Considerations regarding the physical optics, geometric optics, beam propagation parameters, and detail analysis of the effect of imperfections of optical components on the illumination and diffraction beams that need to be accounted for in the modeling of the optical metrology tool and simulations of the diffraction signal to be used in the profile parameter extraction system. For details, refer to FIGS. 4-11B of U.S. Publication No. 2011-0246141, Li, METHOD OF OPTICAL METROLGY OPTIMIZATION USING RAY TRACING, filed Mar. 31, 2010, which is incorporated herein by reference in its entirety.

Figure 4:
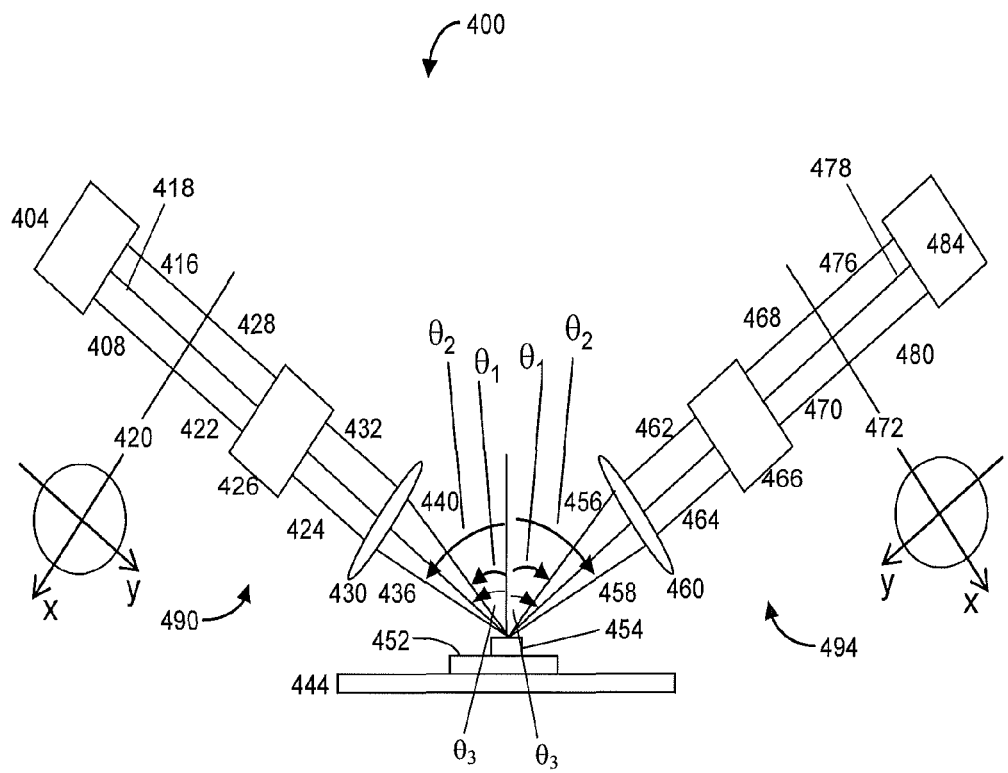
FIG. 4 depicts an exemplary architectural diagram of an optical metrology tool using ray tracing methodology.

FIG. 4 depicts an exemplary architectural diagram of an optical metrology tool using ray tracing methodology. For illustration purposes, only three rays are used, however, the number of rays used in ray tracing can be a single ray, or two or more rays. The optical metrology tool 400 is illustrated using three rays from the light source 404 through optical metrology elements 426 and 430, where the rays are directed to a sample structure 454 on the workpiece 452. The workpiece 452 is disposed on a motion control system 444 which is configured to adjust the focus of the illumination beam onto the workpiece 452. In the current diagram, each ray is traced through all the optical elements in the illumination portion 490 and the detection portion 494 of the optical metrology tool 400 up to and including the detector 484. The first illumination ray 408 originating from the light source 404 is transmitted as a ray 422 through optical element 426, which can include a collimator, polarizer and/or a compensator, generating an output ray 424. The output ray 424 is transmitted to the focusing element 430, generating output ray 436 onto the sample structure 454 at an angle of incidence of $\theta_2$. The second illumination ray 416 proceeds as ray 428, passing through the illumination optical element 426 as output ray 432. As mentioned above, the illumination optical element 426 can include a collimator, polarizer and/or a compensator. The output ray 432 is transmitted to the focusing element 430, generating output ray 440 onto the sample structure 454 at a second angle of incidence of $\theta_1$. The cross-section 420 of the illumination beam consists of many rays, and only representative rays need to be traced through the system. The electric and magnetic field of each ray can be linearly or elliptically polarized, and the position of the rays may be in any location within the cross-section defined by X and Y. The focusing optical element 430 may be a reflective or a refractive optical element.

With reference to FIG. 4, output illumination ray 436 transmitted to the sample structure 454 is diffracted as detection ray 458 at a first diffraction angle the same as the angle of incidence $\theta_2$. The detection ray 458 is transmitted to a collecting optical element 460 generating a detection ray 464, through the collecting optical element 460 as a diffraction ray 464, generating output ray 470, and proceeding as a detection ray 480 onto the detector 484. The collecting optical element 466 may include a collimating lens, compensator and/or a collection polarizer, also referred to as an analyzer. Other optical elements may be included on the detecting portion 494 in order to direct the collection rays onto the detector 484 where detector 484 may comprise one or more detectors to resolve rays angularly such as $\theta_1$ and $\theta_2$, and/or resolve the wavelength of the rays using a dispersion component such as a grating, a monochromator, or a spectrometer. Similarly, output illumination ray 440 is transmitted to the sample structure 454 and diffracted as a detection ray 456 at an angle the same as the first angle of incidence $\theta_1$. The detection ray 456 is transmitted to the collecting optical element 460 generating detection ray 462, through collecting optical element 466, generating ray 468, and proceeding as a detection ray 476 onto the detector 484.

As mentioned above, the collecting optical element 466 may include a collimating lens, compensator and/or a collection polarizer, also called an analyzer. Other optical elements may be included in the detection portion 494 in order to direct the collection ray onto the detector 484 where detector 484 may comprise one or more detectors. The cross-section 472 of the detection beam consists of many rays, and each of the rays can be linearly or elliptically polarized, and the position of the rays may be in any location within the cross-section defined by X and Y. The center ray 418, also known as chief ray, can be traced in the same manner as the first two rays, i.e., through the illumination optical elements, 426 and 430, emerged onto the sample structure 454 at an incident angle $\theta_3$, diffracted at the same angle $\theta_3$ from the sample structure 454 and transmitted through detection optical elements, 460 and 466, and emerged onto the detector 484 as output ray 478. If four rays are used to model the optical metrology tool 400, each of the rays are similarly traced through all of the optical elements in the illumination portion 490 and the detection portion 494 of the optical metrology tool 400 up to and including the detector 484. Similarly, if five rays are used to model the optical metrology tool 400, each of the rays are similarly traced through all of the optical elements in the illumination portion 490 and the detection portion 494 of the optical metrology tool 400 up to and including the detector 484. As mentioned above, the number of rays selected to model the metrology tool 400 can be one or more rays based on the application and objectives of the measurement. As seen in the three-ray example of FIG. 4, the first angle of incidence $\theta_2$ of the output illumination ray 436 on the sample structure 454 on the workpiece 452 can be different for each ray.

FIG. 5 depicts an exemplary architectural diagram 500 illustrating use of a ray tracing model with varying number of rays. Illumination ray 504 is directed at an angle of incidence $\Theta_1$ to the sample structure 524 on a workpiece 520 and is diffracted at an angle $\Theta'_1$ off the sample structure 524 as output ray 504'. The workpiece 520 can be a substrate, wafer, a memory device or the like. Another illumination ray 508 is directed at an angle of incidence $\Theta_2$ to the sample structure 524 on the workpiece 520 and is diffracted at an angle $\Theta'_2$ off the sample structure 524 as output ray 508'. Similarly, illumination rays 512, 516 are directed at an angle of incidence $\Theta_3$, $\Theta_4$ respectively, to the sample structure 524 on the workpiece 520 and are diffracted at an angle $\Theta'_3$, $\Theta'_4$ off the sample structure 524 as output rays 512' and 516' respectively. As mentioned above, the model for ray tracing can utilize one or more rays. In regular ray tracing, the number of rays to be used is pre-selected and the pre-selected number of rays is used to generate the library of simulated diffraction signals. If a different number of rays is used, the library has to be regenerated to utilize the new number of rays. As will be discussed in relation to FIG. 7 to 14 below, the concepts of this invention will provide methods and systems that will eliminate the problems of pre-selected metrology system model parameters.

FIG. 6A depicts an exemplary architectural diagram 600 illustrating use of a ray tracing model with varying tools of different numerical aperture ($NA_1$ vs. $NA_2$). A ray tracing model may utilize an illumination beam comprising two rays directed to a sample structure 624 on a workpiece 604. A diffraction beam off the sample structure 624 comprising two output rays and a numerical aperture, $NA'_1$, which are used to generate a library of simulated diffraction signals (not shown). As mentioned above, the library of diffraction signals can be used to determine one or more profile parameters of the sample structure 624 on the workpiece 604. A different angle of incidence and a different size of numerical aperture, $NA_2$, may be desirable due to changes in the workpiece application, for example, three rays instead of two and different tools, for example, one tool has a numerical aperture size $NA_2$ instead of $NA_1$ of another tool, the configuration of the tool changed by adjustment during preventive maintenance (PM), the library has to be regenerated to utilize the new angle of incidence or the new aperture, $NA_2$. Referring to FIG. 6A, a first ray tracing model comprising rays in the range of the cone C, D, and E are directed to a sample structure 624 on a workpiece 604 at an angle of incidence $\Theta_5$ and a numerical aperture of $NA_1$. The numerical aperture can be a circle, an ellipse, a square or other closed shapes. The rays in the cone C, D, and E are diffracted off the sample structure 624 as diffraction rays in the cone C', D', and E', an angle of diffraction $\Theta'_5$ and a numerical aperture of $NA'_1$. A second ray tracing model comprising rays in cone L, M, and N are directed to the sample structure 624 on the workpiece 604 at an angle of incidence $\Theta_6$ and a numerical aperture of $NA_2$. As before, the numerical aperture can be a circle, an ellipse, a square or other closed shapes. The rays in cone L, M, and N are diffracted off the sample structure 624 as diffraction rays in cone L', M', and N', an angle of diffraction $\Theta'_6$ and a numerical aperture of $NA'_2$. In one embodiment, $NA_1$ can be a minimum numerical aperture and $\Theta_5$ can be the minimum angle of incidence for the range covered by the ray tracing model and $NA_2$ can be a maximum numerical aperture and $\Theta_6$ can be the maximum angle of incidence for the range covered by the ray tracing model. As will be discussed in relation to FIG. 7 to 14 below, the concepts of this invention will provide methods and systems that will address the problems associated with pre-determined number of rays, size of the numerical aperture, angle of incidence, azimuth angle, and the like, in generating a simulated diffraction signal.

FIG. 6B depicts an exemplary architectural diagram 650 illustrating use of a ray tracing model with varying azimuth angle. A ray tracing model for a sample structure (not shown) on a workpiece 654 may utilize one or two rays, a numerical aperture, and an azimuth angle of the illumination beam A at substantially 0, or 45 degrees 658. The ray tracing model and the selected number of rays, numerical aperture, and azimuth angle of substantially 0 or 45 degrees 658 are used to generate a library of diffraction signals. As mentioned above, the library of diffraction signals can be used to determine one or more profile parameters of the sample structure on the workpiece 654. A different azimuth angle may be desirable for the application measured with another tool, such as shown with illumination beam B at an azimuth angle of substantially 46 degrees 662. The library, previously generated with the azimuth angle of substantially 0 or 45 degrees 658, has to be regenerated to use the azimuth angle of substantially 1 or 46 degrees 662. As will be discussed in relation to FIG. 7 to 14 below, the concepts of this invention will provide methods and systems that will address the problems of pre-selected metrology system model parameters.

Typically, several metrology signal parameters such as wavelength range, angle of incidence, azimuth angle, numerical aperture (NA), NA shape, NA position, number of rays, and the like are preselected in order to obtain a reasonable library size, to reduce the training time for a machine learning system (MLS), or both. Examples of metrology signal parameters include reflectance parameter or reflectivity (R), complex Fresnel reflectivities for s-polarized light ($r_s$), complex Fresnel reflectivities for p-polarized light ($r_p$), in phase normalized harmonics ($\alpha$), out phase normalized harmonics ($\beta$), ellipsometer parameters tan ($\psi$) ($\psi$), cos($\Delta$) ($\Delta$), or any combination thereof.

The Jones matrix describes the polarization change of light through various optical elements, where the X and Y components of the complex amplitude of the electric field traveling along the Z-direction. Below is the Jones matrix definition in optical metrology for a completely polarized light beam where the degree of polarization (DOP) of the optical metrology tool is DOP=1:

$$\begin{pmatrix} E_X \\ E_Y \end{pmatrix}_{Output} = J \cdot \begin{pmatrix} E_X \\ E_Y \end{pmatrix}_{Input} \quad (5)$$

where $$J = \begin{pmatrix} J_{SS} & J_{SP} \\ J_{PS} & J_{PP} \end{pmatrix}.$$

where $E_X$ and $E_Y$ are the X and Y components of the amplitude of electric field of light travel along the Z direction and $J_{SS}$, $J_{SP}$, $J_{PS}$, and $J_{PP}$ are complex numbers describing the beam propagation of amplitude of the electric field of light travel along the Z direction.

The other metrology signal parameters such as reflectivity (R), complex Fresnel reflectivities for s-polarized light ($r_s$), complex Fresnel reflectivities for p-polarized light ($r_p$), in phase normalized harmonics ($\alpha$), out phase normalized harmonics ($\beta$), tan($\psi$) ($\psi$), cos($\Delta$) ($\Delta$) are known to people in the art of optical metrology. In order to alleviate the need for regenerating the library due to a change of the metrology signal parameters, there is a need for techniques to maintain the accuracy of determined profile parameters of the sample structure while keeping the size of the library reasonable, reducing the time for training an MLS, or both.

Figure 7:
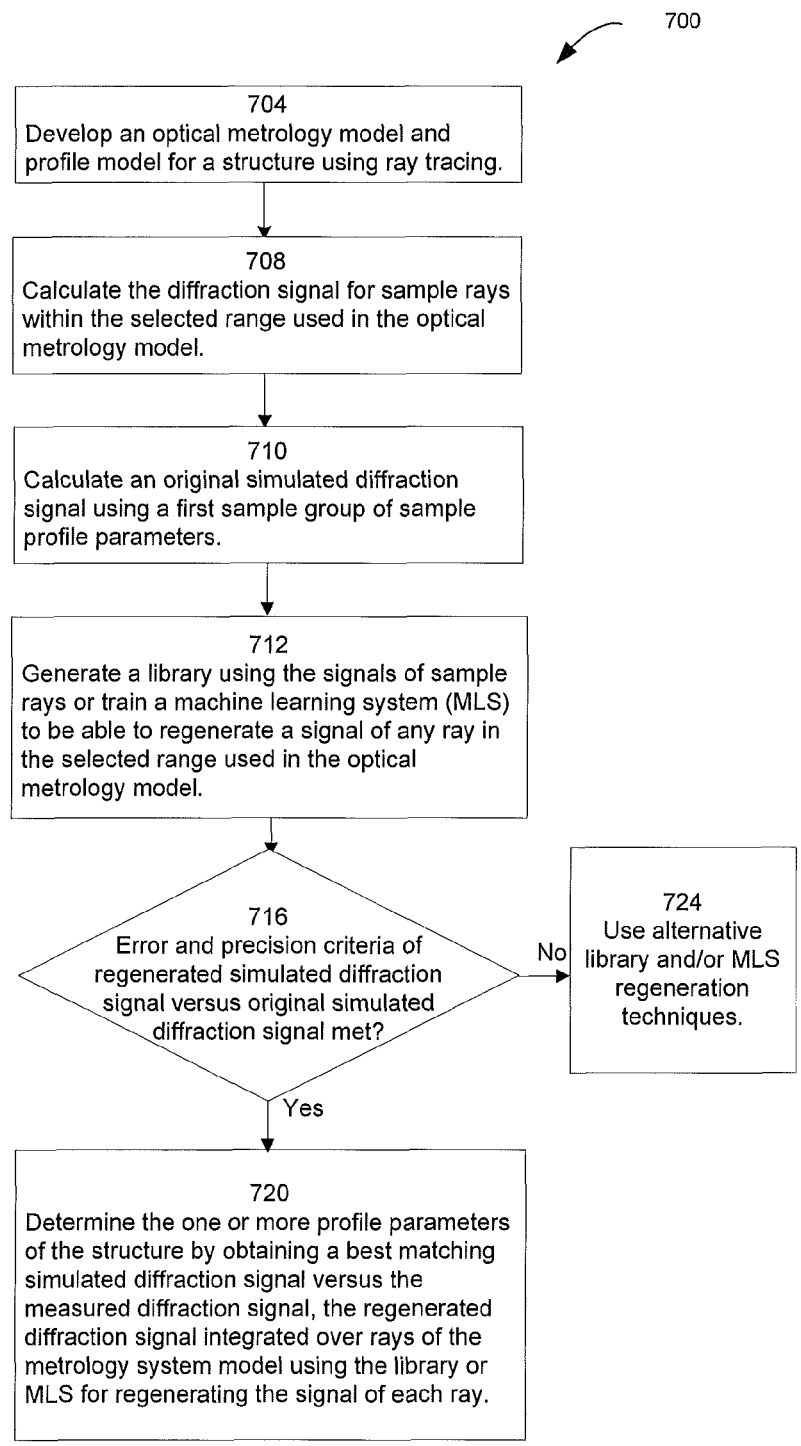
FIG. 7 depicts an exemplary flow chart of a method of generating a library meeting an error and precision criteria, using ray tracing, the library used to determine the profiles of structures formed on a semiconductor wafer, substrate, or workpiece.

FIG. 7 depicts an exemplary flow chart of a method of generating a library meeting an error and precision criteria, using ray tracing, the library used to determine the profiles of structures formed on a semiconductor wafer, substrate, or workpiece. In operation 704, an optical metrology model, including a profile model for a sample structure on a workpiece, is developed. As mentioned above, the workpiece can include a wafer, substrate, memory device and the like. In operation 708, two sample groups of sample profile parameters and beam propagation parameters are pre-determined: a first sample group is used for generating a library or MLS, and a second sample group is used for testing the error and precision of the library or MLS generated. The samples' profile parameters and metrology system model parameters are obtained over the selected one or more profile parameters ranges and over the selected ray position range of the metrology model. In operation 710, an original simulated diffraction signal is calculated using the one or more profile parameters of the first sample group. Calculations of the original simulated diffraction signal may use rigorous couple-wave analysis (RCWA), finite element method, boundary integral elements, momentum method, coordinate transform and/or C method. The C method is an implementation of the Rayleigh expansions of the general grating theory with the assumption that the layer interfaces are flat.

In operation 712, a library including a Jones matrix, a component of the Jones matrix, a Mueller matrix, a component of the Mueller matrix or any two or more combinations thereof, i.e., Jones and/or Mueller matrix or components (JM-MOC), is generated using the first sample group. In one embodiment, an MLS can be trained using the library. Furthermore, the library or MLS is trained in such a way that given any set of one or more profile parameters, or profile within the parameter range of the profile, the library or MLS can regenerate the JMMOC for any ray that is within the selected range of rays in the metrology model. In operation 716, the error and precision of simulated diffraction signals calculated from JMMOCs of the rays using the second sample group are tested by comparing the regenerated simulated diffraction signals with the original simulated diffraction signals, where the original simulated diffraction signals were calculated in operation 710. When the error and precision criteria are met, processing proceeds to operation 720. If the error and precision criteria are not met, processing proceeds to operation 724 where alternative library and/or MLS diffraction signal regeneration techniques can be used. One such technique involves a first library and a difference library discussed in connection with FIG. 8. Other diffraction signal regeneration technologies can also be used.

An error criterion is the deviation of the regenerated simulated diffraction signal compared to the calculated original diffraction signal. Error criterion can include a mean square error, a root mean square error, a sum of squared errors (SSE) or the like. A precision criterion can include repeatability of the measurement using the same metrology tool. The precision criterion can be expressed as a variance from the mean measurement, a standard deviation or percentage from the mean measurement or the like. Use of error and precision criteria for comparing diffraction signals are well known in the art.

Referring to FIG. 7, in operation 720, the simulated diffraction signals that are independent of the number of rays can be used to determine one or more profile parameters of the structure. In one embodiment, the simulated diffraction signal is determined by regenerating the JMMOC for rays that are determined by the metrology model. The JMMOC of the rays of the sample structure are integrated in a metrology model algorithm to simulate the diffraction signal of the metrology system using ray tracing. For a detailed description of generating a simulated diffraction signal using ray tracing, refer to U.S. Patent Publication Nos. 2011-0246141 METHOD OF OPTICAL METROLOGY OPTIMIZATION, by Li, filed on Mar. 31, 2010 and 2011-0246142 OPTIMIZATION OF RAY TRACING AND BEAM PROPAGATION PARAMETERS, by Li, et al., filed on Apr. 1, 2010. In another embodiment, one component of the Jones matrix, the Mueller matrix, or one component of the Mueller matrix or a combination of two or more thereof are regenerated for a sample, one or more profile parameters for the rays determined by the metrology model. A simulated diffraction signal is calculated from the regenerated JMMOC and then compared with the measured diffraction signal, and the one or more profile parameters or profile that generate the best matched simulated diffraction signal are reported as the measured one or more profile parameter or profile of the sample structure. As mentioned above, the MLS can use a neural network, a support vector machine or other machine learning systems techniques.

Figure 8:
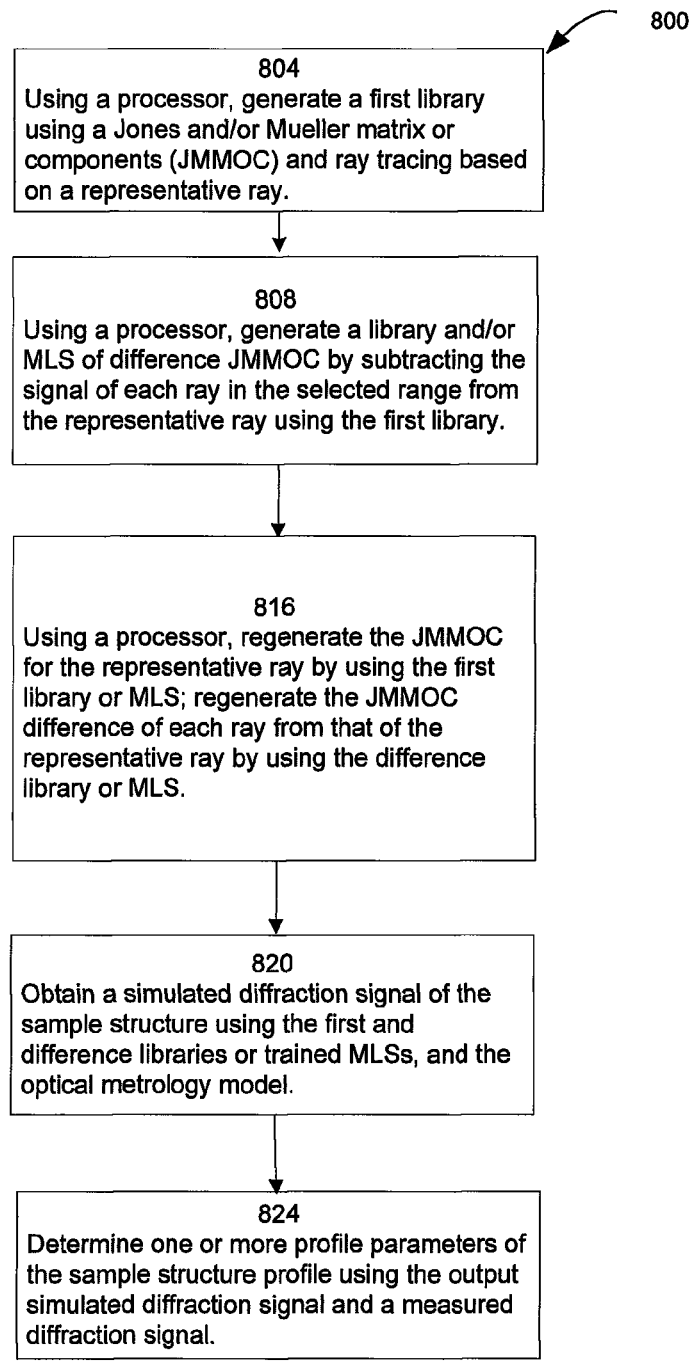
FIG. 8 depicts an exemplary flow chart of a method of generating a difference library that can be utilized to determine the profiles of structures formed on a semiconductor wafer, substrate, or workpiece.

FIG. 8 depicts an exemplary flow chart 800 of a method of generating a difference library which is utilized to determine the one or more profile parameters or profiles of structures formed on a semiconductor wafer, substrate, or workpiece. In operation 804 using a processor, an optical metrology model, including a profile model for the structure, a first library of JMMOC is generated using ray tracing for a selected representative ray, a selected range of a first set of beam propagation parameters, and a selected range of profile parameters or sample profiles. As mentioned above, the first set of beam propagation parameters can include one or more parameters of orientation of the ray such as angle of incidence, azimuth angle, and/or plane of incidence. The first library can be used to train a first MLS in a way that for any sample profile in the selected range of profile parameters, the first MLS can regenerate, for example, the Jones matrix for the ray at the beam propagation parameters determined in operation 804. As mentioned above, the Jones matrix, a component of the Jones matrix, the Mueller matrix, a component of the Mueller matrix, or any combination of the foregoing can be used in the library generation. The selected representative ray can be the chief ray or any ray in the ray tracing model.

In operation 808 using a processor, a first difference library is generated by subtracting each JMMOC of each ray of the set of rays from the JMMOC of the selected representative ray. The difference beam propagation parameters are generated by subtracting the beam propagation parameters of this ray from the propagation parameters of the selected representative ray determined in operation 804. The difference JMMOC is generated by subtracting, for example, the Jones matrix of this ray from the Jones matrix of the selected representative ray that can be regenerated from the first library. The difference library can be used to train an MLS by using the difference beam propagation parameters and the difference JMMOC. The difference MLS is trained in such a way that for any ray with different beam propagation parameters from the selected representative ray, the difference JMMOC can be regenerated, for example, the difference of the Jones matrix from the first library.

Still referring to FIG. 8, in operation 816 using a processor, the JMMOC or more specifically, for example, the Jones matrix, of any ray in the selected range can be regenerated by using the first library generated in operation 804 and the difference library generated in operation 808 in the following way. Assume a three-ray model for ray tracing is used, for example Ray 1 as the representative ray, Ray 2, and Ray 3. First, the first library is used to regenerate the JMMOC for the Ray 1, denoted as $J_a$, for example. Second, the beam propagation parameter difference is calculated by subtracting the beam propagation parameters of a ray from the JMMOC of the selected representative ray. Third, the beam propagation parameter difference and the difference library are used to regenerate the difference of the JMMOC, denoted as $J_n$. Fourth, the JMMOC of the ray is calculated by taking the sum of the diffraction signals of the representative ray, $J_a$, and the difference diffraction signal, $J_n$, of the ray.

To illustrate operation 816 further, a ray, (Ray$_A$), is selected as the selected representative ray and used to generate a first library as described for operation 816 above, so that for each profile of the sample structure or one or more profile parameters of the profile of the structure, a JMMOC can be regenerated. In the example above, the application needs to model Ray 1, Ray 2, and Ray 3. The beam propagation parameter difference is calculated as follows:

$$(\Delta\theta_1, \Delta\phi_1) = [(\theta_1 - \theta_A), (\phi_1 - \phi_A)] \quad (6)$$

where $\theta$ is the angle of incidence and $\phi$ is the azimuth angle of the ray.

The $(\Delta\theta_1, \Delta\phi_1)$ is input into the difference library generated with operation 808 or an MLS generated with operation 808 to generate the difference JMMOC $\Delta J_n$ for the ray, in similar way as in Eq. (6). For example, $(\Delta\theta_1, \Delta\phi_1; \Delta J_1)$ is generated for the Ray 1, $(\Delta\theta_2, \Delta\phi_2; \Delta J_2)$ is generated for the Ray 2, and $(\Delta\theta_3, \Delta\phi_3; \Delta J_3)$ is generated for the Ray 3. If the Jones matrix is selected as the JMMOC, the JMMOC for the rays are calculated as follows:

$$\text{Ray 1: } J_1 = J_a + \Delta J_1 \quad (7)$$

$$\text{Ray 2: } J_2 = J_a + \Delta J_2 \quad (12)$$

$$\text{Ray 3: } J_3 = J_a + \Delta J_3;$$

where $J_a$ is the regenerated JMMOC for the representative ray.

In operation 820, a simulated diffraction signal off the sample structure is determined by using the JMMOC of the sample structure generated in operation 816 using the model of the optical metrology tool and ray tracing. In the example above, the values of $J_1$, $J_2$, and $J_3$ are input into the optical metrology model in order to determine the reflectivity (R), complex Fresnel reflectivities for s-polarized light ($r_s$), complex Fresnel reflectivities for p-polarized light ($r_p$), in phase normalized harmonics ($\alpha$), out phase normalized harmonics ($\beta$), tan($\psi$) ($\psi$), cos($\Delta$) ($\Delta$), or any combination thereof. For a detailed description of generating a simulated diffraction signal using ray tracing, refer to U.S. Patent Publication Nos. 2011-0246141 METHOD OF OPTICAL METROLOGY OPTIMIZATION, by Li, filed on Mar. 31, 2010 and 2011-0246142 OPTIMIZATION OF RAY TRACING AND BEAM PROPAGATION PARAMETERS, by Li, et al., filed on Apr. 1, 2010. The modeled metrology system can be any of the optical metrology systems, for example, a spectroscopic reflectometer or a spectroscopic ellipsometer.

Referring to FIG. 8, in operation 824, one or more profile parameters of the sample structure profile are determined using the simulated diffraction signal of the metrology system obtained in operation 820 that utilized the first library and the difference library or the trained MLS and the trained difference MLS; this is done by determining the best match simulated diffraction signal compared to a measured diffraction signal of the metrology system. The method described with FIG. 8 allows for quick adaptation of the first library to work with the difference library without using a large first library that would anticipate a wide range of numbers of rays. In one embodiment, the number of rays can be 1 to 15 rays. In another embodiment, the selected representative ray is the chief ray and the first library is generated based on the chief ray.

Figure 9:
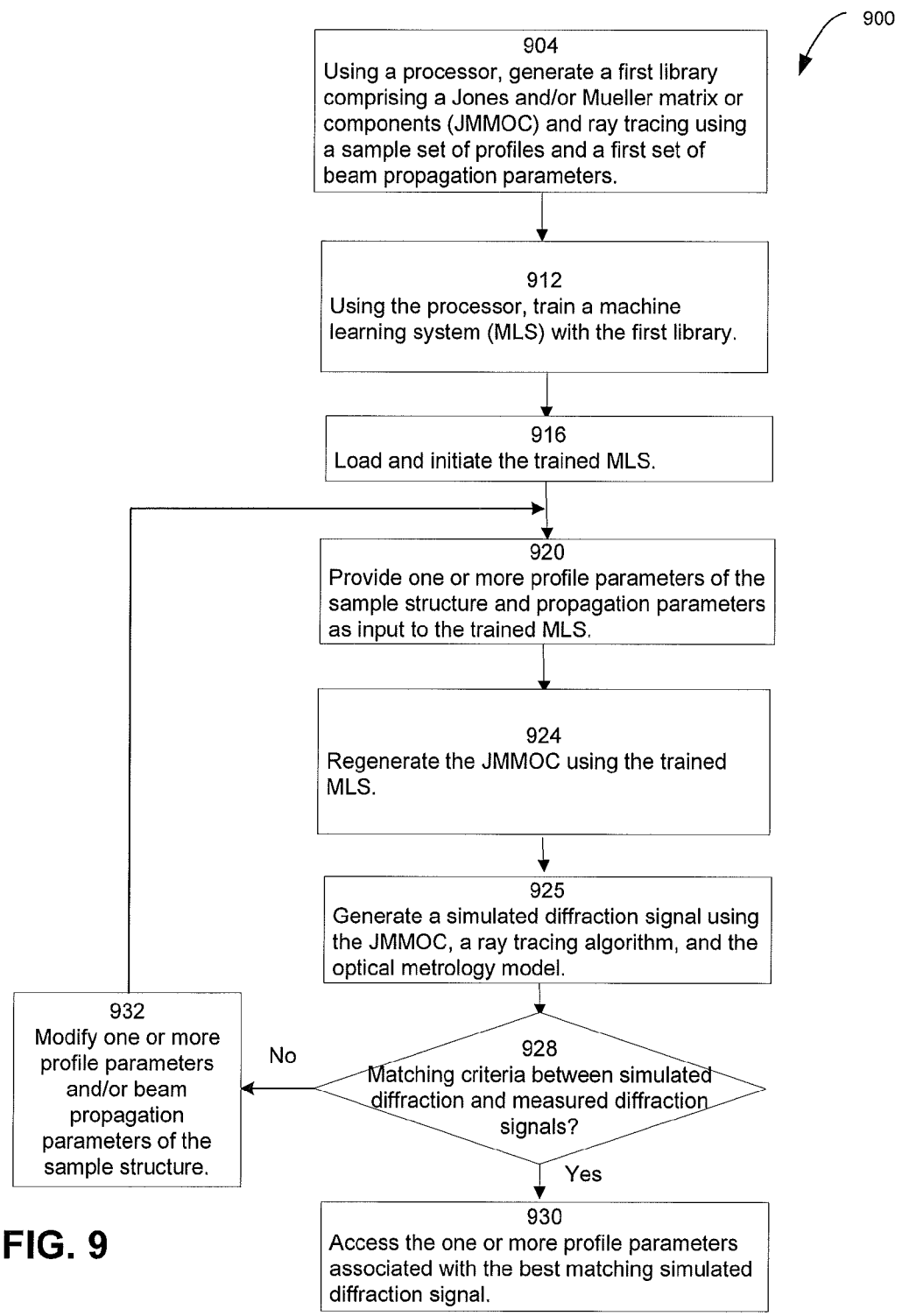
FIG. 9 depicts an exemplary flow chart of a method of regenerating a diffraction signal using a trained MLS to determine the profiles of structures formed on a semiconductor wafer, substrate, or workpiece.

FIG. 9 depicts another exemplary flow chart 900 of a method of regenerating a JMMOC using a trained MLS which is utilized to determine the one or more profile parameters or profiles of a sample structure formed on a semiconductor wafer, substrate, or workpiece. In operation 904 using a processor, a library comprising a JMMOC is generated for the sample structure using ray tracing, beam propagation parameters, a training sample set of one or more profile parameters or profile of the sample structure.

In operation 912 using the processor, the relationship between the beam propagation parameters and the JMMOC generated using the training sample set are used to train an MLS to use one or more profile parameters and beam propagation parameters as input and a regenerated JMMOC as output. For example, the input for MLS training can be one or more profile parameters comprising a sidewall angle of ~90 degrees, top critical dimension (CD) of 20 nanometers, and an angle of incidence of 65 degrees, and an azimuth angle of 0 degrees as beam propagation parameters. The output of the MLS can be a Jones matrix for the set of parameters provided as input. As mentioned above, the MLS can use a neural network, a support vector machine or other machine learning systems techniques. In operation 916, the trained MLS is loaded and initiated. In operation 920, one or more profile parameters of the sample structure of the profile model and one or more beam propagation parameters are provided as input to the trained MLS. In operation 924, the trained MLS regenerates JMMOC as output. In operation 925, the regenerated JMMOC are input to a metrology system model, after calculations, the metrology system model generates an output simulated diffraction signal. In operation 928, if the matching criteria between the simulated diffraction signal of the metrology system model and the measured diffraction signal are not met, one or more input profile parameters of the sample structure and/or one or more beam propagation parameters are adjusted and operations 920, 924, 925, 928, and 932 are iterated until the matching criteria between the simulated diffraction signal and the measured diffraction signal are met. The matching criteria can include goodness of fit (GOF), cost function, sum-squared-error (SSE), weighted cost function, and the like. When the matching criteria are met, in operation 930, the one or more profile parameters associated with the best match simulated diffraction signal of the metrology system model are considered as the one or more profile parameters of the measured diffraction signal.

In one embodiment, in operation 912, the predetermined sampling set is used to train an MLS to use one or more profile parameters and one or more beam propagation parameters as input and a JMMOC as output. In this embodiment, operations 920 and 924 work together to regenerate the JMMOC with the trained MLSs in 2 milliseconds or less.

Figure 10:
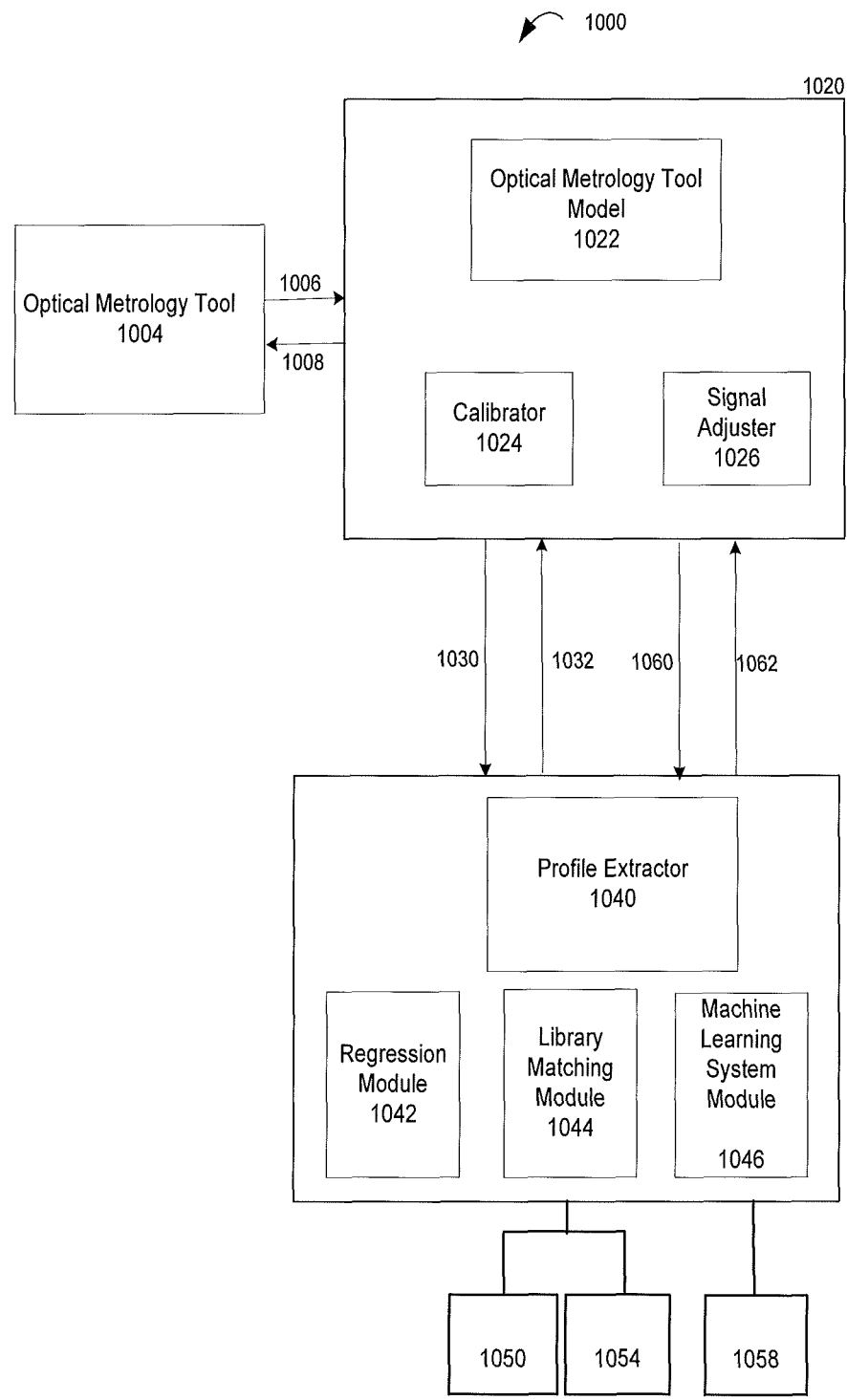
FIG. 10 depicts an exemplary architectural diagram of a system illustrating use of a ray tracing model to generate a representative library and a difference library to determine the profiles of structures formed on a semiconductor wafer, substrate, or workpiece.

FIG. 10 depicts an exemplary architectural diagram 1000 of a system illustrating use of ray tracing model to generate a first library 1050 and a difference library 1054. The system 1000 is used for determining profile parameters using an optical metrology tool 1004, ray tracing, and use of a first 1050 and a difference library 1054. The optical metrology tool 1004 is calibrated using the specifications from the optical metrology tool vendor and the calibrator 1024 in the processor 1020, generating a metrology system model (not shown) and calibration parameters. An optical metrology tool model 1022 is generated using the processor 1020, using the specifications of the optical metrology tool 1004 and specific operating settings of the optical metrology tool 1004 required for the application, for example, angle of incidence, numerical aperture, and azimuth angle. The optical metrology tool model 1022 includes characterization of the illumination beam, including range of wavelengths, the number of rays for ray tracing, the beam propagation parameters, for example, angle of incidence and azimuth angle, other calibration parameters and the like. Information 1006 regarding the structure (not shown) being measured is sent from the optical metrology tool 1004 to the signal adjuster 1026 in the processor 1020. The signal adjuster 1026 uses the optical metrology tool model 1022 and calibration parameters to convert the measured signal to an adjusted metrology output signal 1030 that is transmitted to the profile extractor 1040. The profile extractor can use a regression module 1042, a library matching module 1044, and/or a machine learning system (MLS) module 1046 to determine the desired one or more profile parameters 1032 of the structure to the processor 1020. The library module can include a first library 1050 of JMMOC based on the selected representative ray and a difference library 1054 generated using the difference between the diffraction signal for each of the rays and the diffraction signal for the selected representative ray. The trained MLS can utilize a neural network, a support vector machine methodology, or other machine learning techniques.

In another embodiment, the first library 1050 and difference library 1054 can be used to train an MLS 1058 which can be used to determine one or more profile parameter of the sample structure. The JMMOC of the sample structure regenerated from the libraries, 1050 and 1054, are sent to the processor 1020 as the data set 1062. The processor 1020 then calculates, using the JMMOC of the sample structure, an output simulated diffraction signal of the metrology system by using the calibrated system parameters and the optical metrology model. Calibrated system parameters comprise angle of incidence, numerical aperture, analyzer angle, and the like. The diffraction signal of the metrology system 1060 has the same format as the measured diffraction signal 1030. The measured diffraction signal 1030 and the diffraction signal 1060 are then sent to the profile extractor 1040 for determining one or more parameters of the sample structure. The processor 1020 transmits feedback data 1008 such as information to change adjustable variables of the optical metrology tool 1004.

Figure 11:
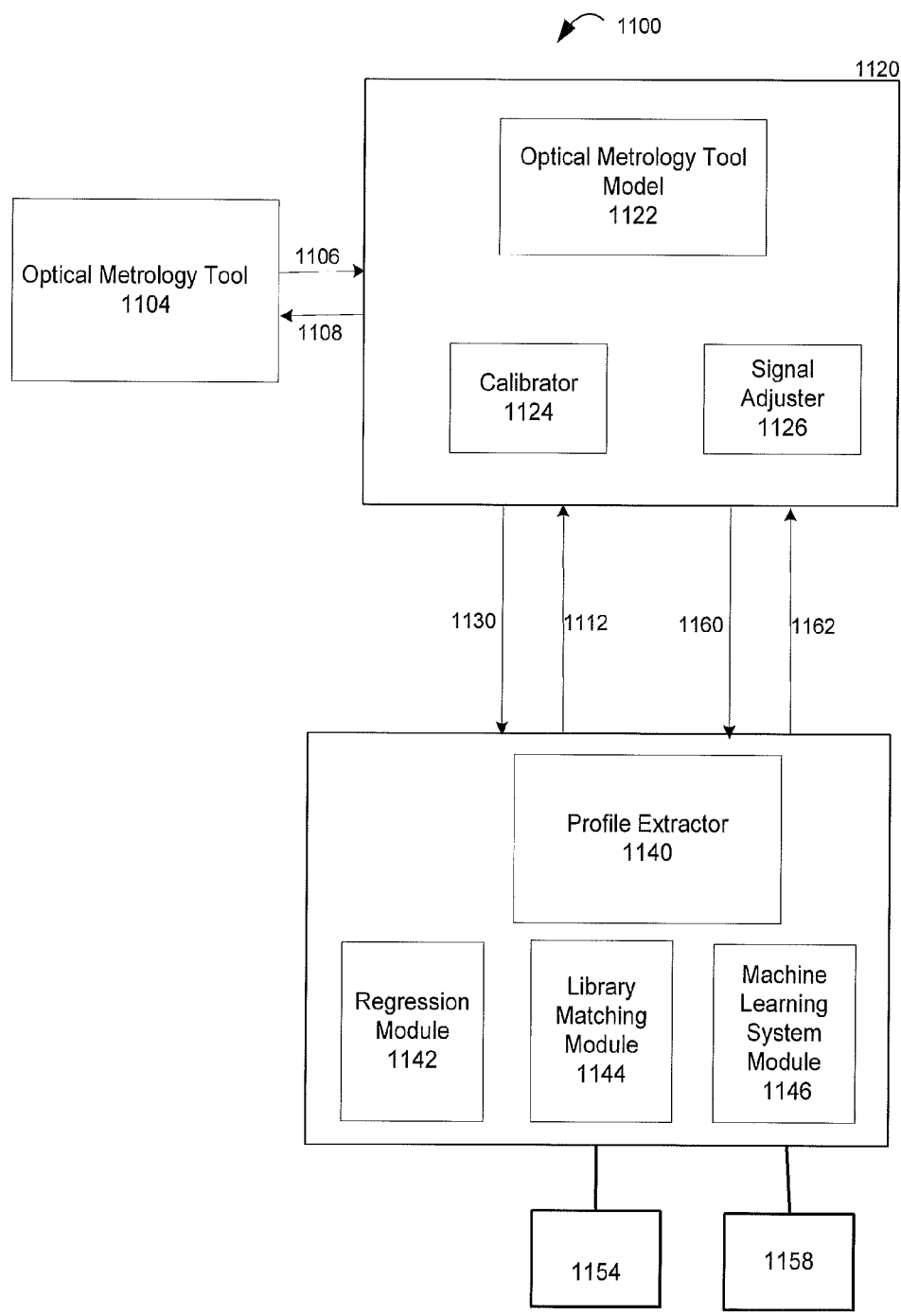
FIG. 11 depicts an exemplary architectural diagram of a system illustrating use of a ray tracing model to regenerate a simulated diffraction signal using a trained MLS to determine the profiles of structures formed on a semiconductor wafer, substrate, or workpiece.

FIG. 11 depicts an exemplary architectural diagram of a metrology system 1100 illustrating use of ray tracing model to generate a diffraction signal of the metrology system 1100 using a trained MLS 1158 and determine one or more profile parameters of sample structure. The metrology system 1100 is used for determining profile parameters using an optical metrology tool 1104, ray tracing algorithms, and use of a first library 1154 based on first ranges of beam propagation parameters. The optical metrology tool 1104 is calibrated using the specifications from the optical metrology tool vendor and the calibrator 1124 in the processor 1120, generating a metrology system model 1122 and calibration parameters. An optical metrology tool model 1122 is generated using the processor 1120, using the specifications of the optical metrology tool 1104 and specific operating settings of the optical metrology tool 1104 required for the application, for example, wavelength range, angle of incidence, numerical aperture, azimuth angle, and the kind. The optical metrology tool model 1122 includes characterization of the illumination beam, including range of wavelengths, the number of rays used in the ray tracing model, the beam propagation parameters, for example, angle of incidence and azimuth angle, calibration parameters and the like. Information 1106 regarding the sample structure (not shown) being measured is sent from the optical metrology tool 1104 to the signal adjuster 1126 in the processor 1120. The signal adjuster 1126 uses the optical metrology tool model 1122 and calibration parameters to convert the measured signal to an adjusted metrology output diffraction signal 1130 that is transmitted to the profile extractor 1140.

The profile extractor can use a regression module 1142, a library matching module 1144, and/or a machine learning system (MLS) module 1146 to determine the desired one or more profile parameters 1162 of the sample structure to the processor 1120. The library module 1144 can include a first library 1154 of JMMOC of the sample structure and corresponding one or more profile parameters of the structure. The MLS module 1146 can use the first library 1154 to train MLS 1158 to regenerate the JMMOC based on the one or more profile parameters and a first set of beam propagation parameters. The MLS 1158 can utilize neural net or support vector machine methodology or other machine learning system techniques. One or more profile parameters and beam propagation parameters are used as input to the trained MLS 1158 to regenerate an output diffraction signal of the sample structure. The diffraction signal of the sample structure regenerated from the MLS 1158 is sent to the processor 1120 as the data set 1162. The processor 1120 then convert the diffraction signal of the sample structure into the diffraction signal of the metrology system by using the calibrated system parameters and optical metrology tool model 1122. Calibrated system parameters comprise angle of incidence, numerical aperture, analyzer angle, and the like. The simulated diffraction signal of the metrology system 1160 has the same format as the measured diffraction signal 1130. The measured diffraction signal 1130 and the output simulated diffraction signal 1160 are then sent to the profile extractor 1140 for determining one or more parameters of the sample structure that best matches the measured diffraction signal according to the matching criteria. The matching criteria can include goodness of fit (GOF), cost function, sum-squared-error (SSE), weighted cost function, and the like. The processor 1120 transmits feedback data 1108 such as information to change adjustable variables of the optical metrology tool 1104.

Figure 12:
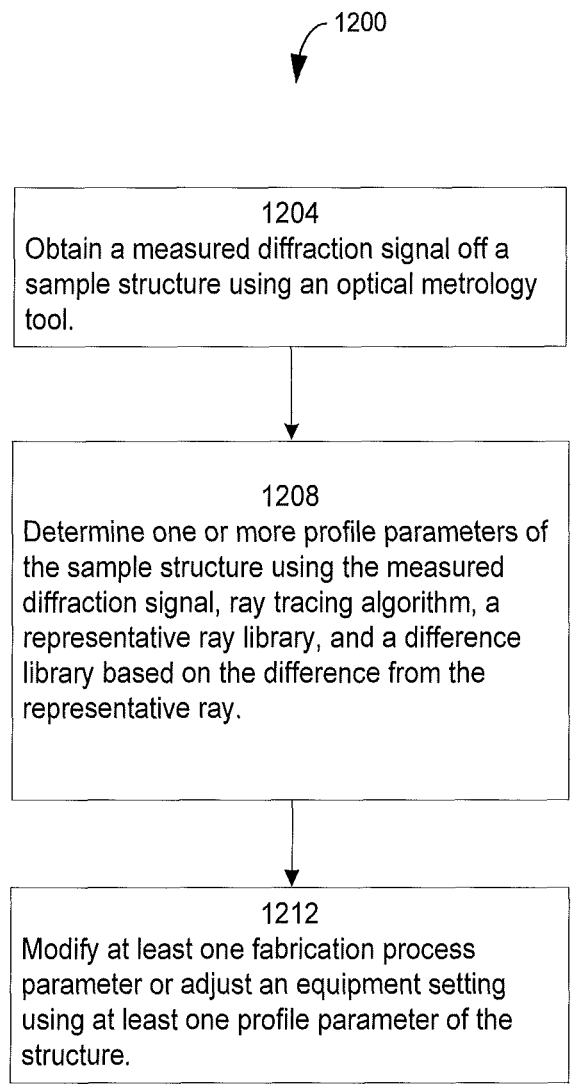
FIG. 12 depicts an exemplary flowchart for a method of controlling a fabrication process utilizing a selected representative ray library and a difference library to determine the profile parameters of structures formed on a semiconductor wafer, substrate, or workpiece.

FIG. 12 depicts an exemplary flowchart 1200 for a method of controlling a fabrication process utilizing profile parameters. In operation 1204, a measured diffraction signal off the sample structure is obtained using an optical metrology tool. In operation 1208, one or more profile parameters of the sample structure are determined using the measured diffraction signal, ray tracing algorithm, and metrology system model, a selected representative ray library, and a difference library based on the selected representative ray. The operations to generate the selected representative ray library based on the selected representative ray and generate the difference library based on the selected representative ray is similar to the method operations illustrated and described in connection with FIG. 8. In operation 1212, at least one fabrication process parameter of a fabrication cluster is modified or at least one equipment setting of the fabrication cluster is adjusted based on the determined one or more profile parameter. The fabrication cluster can include an etch, track, dry etch, wet etch, deposition, cleaning, chemical-mechanical planarization, temperature process systems, and the like. A fabrication process parameter includes etchant flow rate, pressure, temperature, bake time, dose, exposure, and the like.

Figure 13:
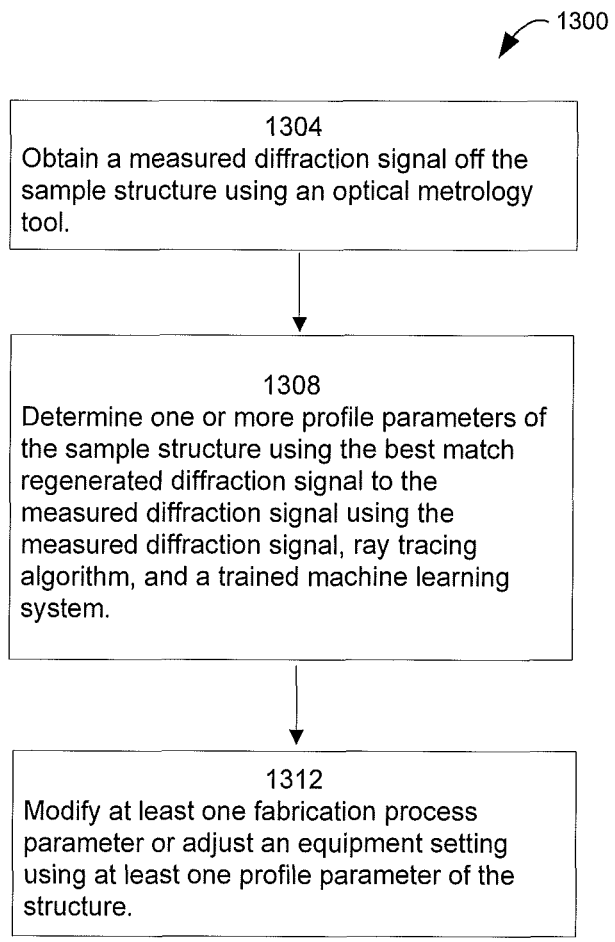
FIG. 13 is another exemplary flowchart for a method of controlling a fabrication process utilizing a trained MLS to regenerate a best match output diffraction signal to the measured diffraction signal for determining profile parameters of structures formed on a semiconductor wafer, substrate, or workpiece.

FIG. 13 is another exemplary flowchart 1300 for a method of controlling a fabrication process utilizing one or more profile parameters. In operation 1304, a measured diffraction signal off the sample structure is obtained using an optical metrology tool. In operations 1308, a simulated diffraction signal is generated from JMMOC obtained using a library or trained MLS. In operation 1312, one or more profile parameters of the sample structure are determined using the best match simulated diffraction signal compared to the measured diffraction signal using a ray tracing algorithm and one or more libraries or one or more trained MLSs. Operations for this procedure are similar to the operations described in connection with FIG. 7 and FIG. 9. With regards to the method described in connection with FIG. 7, a library or a trained MLS is generated to regenerate a JMMOC of any ray in the selected range used in the optical metrology model. If the error and precision criteria of the regenerated JMMOC are met, one or more profile parameters of the sample structure are determined by obtaining a best matching regenerated simulated diffraction signal versus the measured diffraction signal.

Still referring to FIG. 13 and operation 1308, with regards to the method described in connection with FIG. 9, an MLS is trained using JMMOC for a sample set of rays in the selected range of rays used for ray tracing and a set of beam propagation parameters. The trained MLS is loaded and initiated, and input comprising one or more profile parameters of the sample structure and beam propagation parameters are provided. An output JMMOC is regenerated by the trained MLS. The regenerated JMMOC is used by the optical metrology model to generate a simulated diffraction signal. A best match simulated diffraction signal is obtained and the one or more profile parameters of the best matching simulated diffraction signal are accessed and used for process control. In operation 1312, at least one fabrication process parameter of a fabrication cluster is modified or at least one equipment setting of the fabrication cluster is adjusted based on the determined one or more profile parameter. The fabrication cluster can include an etch, track, dry etch, wet etch, deposition, cleaning, chemical-mechanical planarization, temperature process systems, and the like. A fabrication process parameter includes etchant flow rate, pressure, temperature, bake time, dose, exposure, and the like.

In one embodiment, where the JMMOC uses the Jones matrix or a component of the Jones matrix, in operation 1308, one or more profile parameters of the sample structure are determined using the best match simulated diffraction signal to the measured diffraction signal using the trained MLS and metrology system model to generate the simulated diffraction signal. In this embodiment, operations 1308 is configured to require 2 milliseconds or less. The operations to generate the first library used to train the MLS are similar to the method illustrated and described in connection with FIG. 9. In other embodiments, the JMMOC utilizes the Mueller matrix, one component of the Jones matrix, one component of the Mueller matrix, or any combination thereof.

Figure 14:
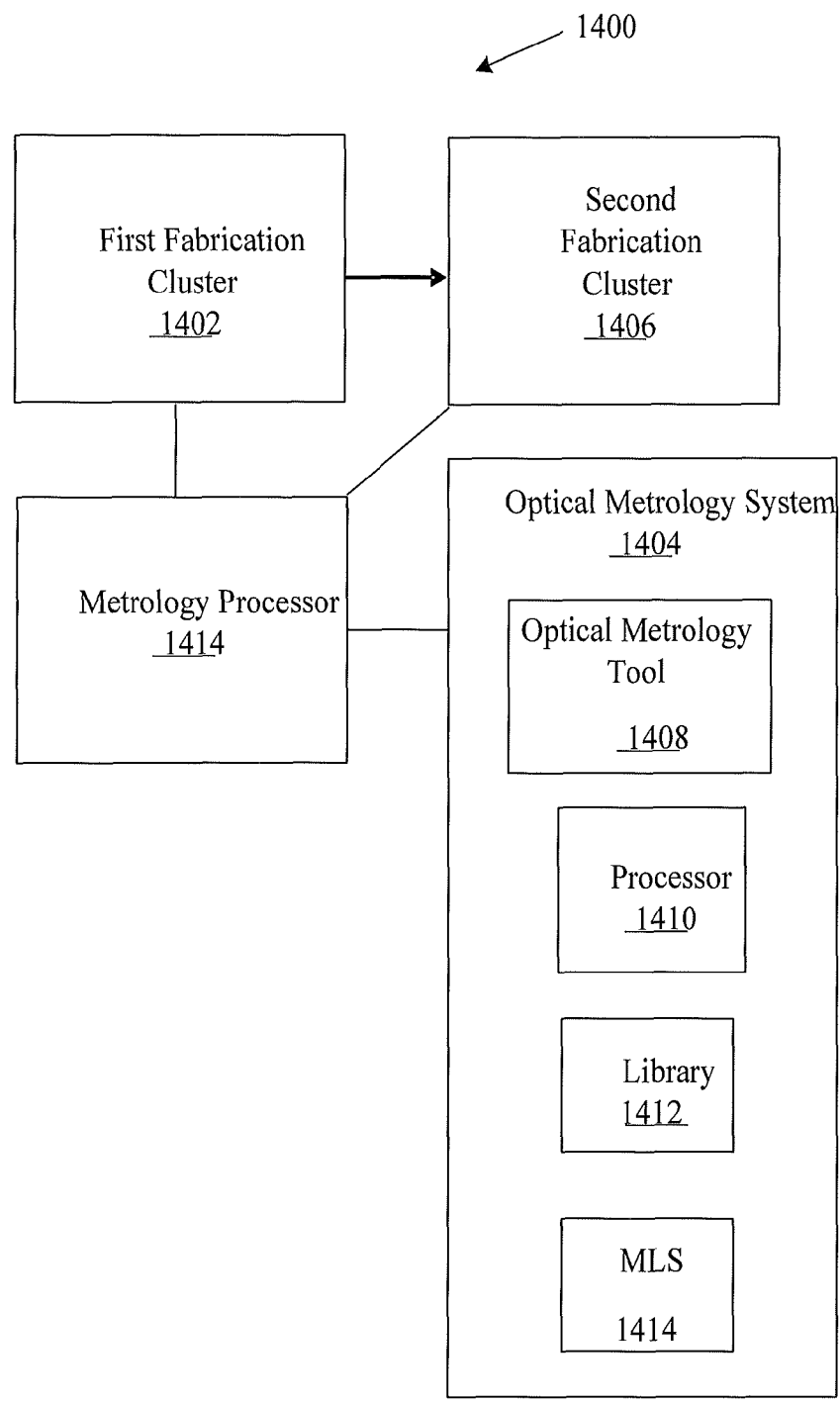
FIG. 14 is an exemplary block diagram of a system for determining and utilizing profile parameters for process and equipment control.

FIG. 14 is an exemplary block diagram of a system 1400 for determining and utilizing profile parameters for automated process and equipment control. System 1400 includes a first fabrication cluster 1402 and optical metrology system 1404. System 1400 also includes a second fabrication cluster 1406. Although the second fabrication cluster 1406 is depicted in FIG. 14 as being subsequent to first fabrication cluster 1402, it should be recognized that second fabrication cluster 1406 can be located prior to first fabrication cluster 1402 in system 1400, for example, in the manufacturing process flow.

A photolithographic process, such as exposing and/or developing a photoresist layer applied to a wafer, can be performed using first fabrication cluster 1402. Optical metrology system 1404 is similar to optical metrology system 40 of FIG. 1. In one exemplary embodiment, optical metrology system 1404 includes an optical metrology tool 1408 and processor 1410. Optical metrology tool 1408 is configured to measure a diffraction signal off the sample structure. Processor 1410 is configured to use the measured diffraction signal measured by the optical metrology tool, adjust using the signal adjuster (1126 in FIG. 11), and generate an adjusted metrology output signal. Furthermore, processor 1410 is configured to compare the adjusted metrology output signal to a simulated diffraction signal. As mentioned above, the simulated diffraction signal is determined using an optical metrology tool model using ray tracing, a set of profile parameters of the sample structure and numerical analysis based on the Maxwell equations of electromagnetic diffraction. In one exemplary embodiment, optical metrology system 1404 can also include a library 1412 with a plurality of diffraction signals and a plurality of values of one or more profile parameters associated with the plurality of diffraction signals. As described above, the library can be generated in advance; metrology processor 1410 can compare an adjusted metrology output signal to the plurality of simulated diffraction signals in the library. When a matching simulated diffraction signal is found, the one or more values of the profile parameters associated with the matching simulated diffraction signal in the library are assumed to be the one or more values of the profile parameters used in the wafer application to fabricate the sample structure.

System 1400 also includes a metrology processor 1416. In one exemplary embodiment, processor 1410 can transmit the one or more values of the one or more profile parameters to metrology processor 1416. Metrology processor 1416 can then adjust one or more process parameters or equipment settings of the first fabrication cluster 1402 based on the one or more values of the one or more profile parameters determined using optical metrology system 1404. Metrology processor 1416 can also adjust one or more process parameters or equipment settings of the second fabrication cluster 1406 based on the one or more values of the one or more profile parameters determined using optical metrology system 1404. As noted above, second fabrication cluster 1406 can process the wafer before or after fabrication cluster 1402. In another exemplary embodiment, processor 1410 is configured to train machine learning system 1414 using the set of regenerated JMMOC and beam propagation parameters as inputs to machine learning system 1414 and profile parameters as the expected outputs of machine learning system 1414.

Although exemplary embodiments have been described, various modifications can be made without departing from the spirit and/or scope of the present invention. New, revised, or enhanced mathematical expressions similar to the Jones and Mueller matrices can be used to generate and regenerate JMMOCs. For example, other techniques of partitioning libraries to focus on a major dimension of diffraction data can be used to create sub-libraries that can be used to train MLSs. Two or more MLSs can be used to determine profile parameters of a complex structure such a multiple three-dimensional features in a repeating structure. For automated process control, the fabrication clusters may be a track, etch, deposition, chemical-mechanical polishing, thermal, or cleaning fabrication cluster. Therefore, the present invention should not be construed as being limited to the specific forms shown in the drawings and described above.

What is claimed:

1. A method for enhancing accuracy of an optical metrology system, the optical metrology system including an optical metrology tool, an optical metrology model, and a profile extraction algorithm, the optical metrology model including a model of the optical metrology tool and a profile model of the sample structure; the sample structure formed on a substrate, the profile model having profile parameters, the optical metrology model having an illumination beam, the method comprising:

(a) using a processor, generating a library comprising Jones and/or Mueller matrices or components (JMMOC) and corresponding profile parameters, the library generated using ray tracing and a selected range of beam propagation parameters in the optical metrology model;

(b) obtaining a measured diffraction signal off the sample structure using the optical metrology tool; and (c) calculating an original simulated diffraction signal for the sample structure using the optical metrology model;

(d) setting an error and precision criteria for a regenerated simulated diffraction signal;

(e) if the error and precision criteria for the regenerated simulated diffraction signal compared to the original simulated diffraction signal are met:

(e1) obtaining a simulated diffraction signal of the sample structure using regenerated JMMOC of all rays determined by the optical metrology model;

(e2) integrating regenerated JMMOC of the rays in the optical metrology model, generating a simulated diffraction signal;

(e3) determining one or more profile parameters of the sample structure using the measured diffraction signal, the simulated diffraction signal, and a matching algorithm.

2. The method of claim 1 wherein the JMMOC is a Jones matrix or two or more components of the Jones matrix.

3. The method of claim 1 wherein the JMMOC is a Mueller matrix or two or more components of the Mueller matrix.

4. The method of claim 1 wherein the JMMOV is a Jones matrix and a Mueller matrix.

5. The method of claim 1 wherein the MLS uses a neural net or a support vector machine.

6. The method of claim 1 wherein the angle of incidence of the illumination beam in the optical metrology model is variable.

7. The method of claim 1 wherein the azimuth angle of the illumination beam in the optical metrology model is variable.

8. The method of claim 1 wherein the angle of incidence and the azimuth angle of the illumination beam in the optical metrology model are variables.

9. The method of claim 1 wherein the number rays in numerical aperture in the optical metrology model is variable.

10. The method of claim 1 wherein the angle of incidence, the azimuth angle, and the numerical aperture of the illumination beam in the optical metrology model are variables.

11. The method of claim 1 wherein iterations of operations to regenerate the JMMOC requires 2 milliseconds or less.

12. The method of claim 1 further comprising:

accessing one or more profile parameters of the output diffraction signal matching the measured diffraction signal;

storing the accessed one or more profile parameters.

13. A method of enhancing accuracy of an optical metrology system including an optical metrology tool and an optical metrology model, the optical metrology model including a model of the optical metrology tool and a profile model of a sample structure; the sample structure formed on a substrate, the profile model having profile parameters, the optical metrology tool having an illumination beam, the illumination beam having an angle of incidence and an azimuth angle, the method comprising:

(a) using a processor, generating a first library comprising Jones and/or Mueller matrices or components (JMMOC) and corresponding profile parameters, the library generated using ray tracing and a first set of beam propagation parameters;

(b) using the processor, training a machine learning system (MLS) using the first library, with one or more profile parameters and beam propagation parameters as input and corresponding JMMOC as output;

(c) loading and initiating the MLS;

(d) providing one or more profile parameters and a range of beam propagation parameters to the MLS as input;

(e) regenerating the corresponding JMMOC as output of the trained MLS;

(f) generating a simulated diffraction signal using the regenerated JMMOC, a ray tracing algorithm, and the optical metrology model;

(g) if matching one or more criteria of the simulated diffraction signal compared to a measured diffraction signal are met, accessing the one or more profile parameter associated with the matching simulated diffraction signal;

else, modifying the one or more profile parameters and/or the range of beam propagation parameters and iterating operations (d), (e), (f), and (g) until the matching one or more criteria are met.

14. The method of claim 13 wherein the JMMOC includes two or more components of the Jones matrix.

15. The method of claim 13 wherein the JMMOC includes two or more components of the Mueller matrix.

16. The method of claim 13 wherein the JMMOC includes two or more components of the Jones and the Mueller matrix.

17. The method of claim 13 wherein the JMMOC includes a Jones matrix, a Mueller matrix, a component of the Jones matrix, a component of the Mueller matrix, or combinations of two or more thereof.

18. The method of claim 13 wherein the MLS uses a neural net methodology or a support vector machine.

19. The method of claim 13 wherein operations (d) and (e) requires 2 milliseconds or less.

20. The method of claim 13 wherein the matching one or more criteria includes an error and an accuracy criteria.

* * * * *